United States Patent
Picciotto et al.

(10) Patent No.: US 11,444,213 B2
(45) Date of Patent: Sep. 13, 2022

(54) RADIATION DETECTOR AND RADIATION DETECTION APPARATUS

(71) Applicants: FONDAZIONE BRUNO KESSLER, Trento (IT); HORIBA, Ltd., Kyoto (JP)

(72) Inventors: Antonino Picciotto, Trento (IT); Francesco Ficorella, Trento (IT); Nicola Zorzi, Trento (IT); Daisuke Matsunaga, Kyoto (JP); Kengo Yasui, Kyoto (JP)

(73) Assignees: FONDAZIONE BRUNO KESSLER, Trento (IT); HORIBA, LTD., Kyoto (JP)

( * ) Notice: Subject to any disclaimer, the term of this patent is extended or adjusted under 35 U.S.C. 154(b) by 399 days.

(21) Appl. No.: 16/614,948

(22) PCT Filed: May 28, 2018

(86) PCT No.: PCT/JP2018/020376
§ 371 (c)(1),
(2) Date: Nov. 19, 2019

(87) PCT Pub. No.: WO2018/225563
PCT Pub. Date: Dec. 13, 2018

(65) Prior Publication Data
US 2020/0183024 A1  Jun. 11, 2020

(30) Foreign Application Priority Data
Jun. 5, 2017  (JP) .............................. JP2017-110697

(51) Int. Cl.
*G01T 1/24* (2006.01)
*G01T 1/02* (2006.01)
(Continued)

(52) U.S. Cl.
CPC .... *H01L 31/022416* (2013.01); *A61B 6/4208* (2013.01); *G01N 23/203* (2013.01);
(Continued)

(58) Field of Classification Search
CPC .......... A61B 6/06; A61B 6/42; A61B 6/4206; G01N 23/20; G01N 23/20008;
(Continued)

(56) References Cited

U.S. PATENT DOCUMENTS 7,705,301 B2 * 4/2010 Tseng .................. G01N 23/225
250/311
2013/0277555 A1 10/2013 Kooijman et al.
(Continued)

FOREIGN PATENT DOCUMENTS

JP  S53-66158 U  6/1978
JP  H06-68831 A  3/1994
(Continued)

OTHER PUBLICATIONS

International Search Report dated Aug. 21, 2018 for PCT/JP2018/020376 and English translation.

*Primary Examiner* — Anastasia Midkiff
(74) *Attorney, Agent, or Firm* — Lucas & Mercanti, LLP

(57) ABSTRACT

Provided are a radiation detector and a radiation detection apparatus in which the efficiency of detecting radiation is enhanced by increasing a portion capable of detecting radiation. A radiation detector includes a semiconductor part having a plate-like shape, the semiconductor part being provided with a through hole penetrating the semiconductor part, one surface of the semiconductor part being an incident surface for radiation. The semiconductor part has a sensitive portion capable of detecting incident radiation, the sensitive portion including an inner edge of the incident surface.

11 Claims, 8 Drawing Sheets

(51) Int. Cl.
    *H01J 37/244*    (2006.01)
    *H01L 31/0224*   (2006.01)
    *G01N 23/203*    (2006.01)
    *A61B 6/00*      (2006.01)
    *G01N 23/207*    (2018.01)
    *H01L 27/146*    (2006.01)
    *H01L 27/14*     (2006.01)
    *H01L 31/0352*   (2006.01)
    *G01N 21/47*     (2006.01)

(52) U.S. Cl.
CPC .......... *G01N 23/207* (2013.01); *G01T 1/241* (2013.01); *G01T 1/244* (2013.01); *H01J 37/244* (2013.01); *H01L 27/14* (2013.01); *H01L 27/14603* (2013.01); *H01L 27/14607* (2013.01); *H01L 31/0352* (2013.01); *G01N 2021/4716* (2013.01); *G01N 2223/50* (2013.01); *G01T 1/026* (2013.01); *H01J 2237/032* (2013.01); *H01J 2237/2442* (2013.01); *H01J 2237/2446* (2013.01); *H01J 2237/2448* (2013.01); *H01L 31/0224* (2013.01)

(58) Field of Classification Search
CPC .......... G01N 23/20058; G01N 23/203; G01N 23/205; G01N 23/207; G01N 23/22; G01N 23/223; G01N 37/00; G01N 2201/00; G01N 2201/02; G01N 2201/022; G01N 2021/1765; G01N 2021/177; G01N 2021/1772; G01N 2021/4709; G01N 2021/4716; G01N 2223/05; G01N 2223/07; G01N 2223/30; G01N 2223/308; G01N 2223/40; G01N 2223/50; G01T 1/02; G01T 1/026; G01T 1/1614; G01T 1/1618; G01T 1/24; G01T 1/241; G01T 1/243; G01T 1/244; G01T 7/00; H01J 35/16; H01J 35/18; H01J 37/02; H01J 37/09; H01J 37/147; H01J 37/16; H01J 37/22; H01J 37/244; H01J 2237/03; H01J 2237/032; H01J 2237/045; H01J 2237/0451; H01J 2237/244; H01J 2237/2441; H01J 2237/24415; H01J 2237/2442; H01J 2237/2446; H01J 2237/24475; H01J 2237/2448; H01L 27/14; H01L 27/144; H01L 27/146; H01L 27/14601; H01L 27/14603; H01L 27/14607; H01L 27/14618; H01L 27/15; H01L 31/0224; H01L 31/022416; H01L 31/0248; H01L 31/0352

See application file for complete search history.

(56) References Cited

U.S. PATENT DOCUMENTS

| | | | | |
|---|---|---|---|---|
| 2014/0197310 | A1* | 7/2014 | Hill | G01N 23/2254 |
| | | | | 250/307 |
| 2017/0047192 | A1* | 2/2017 | Frosien | H01J 37/28 |
| 2017/0236683 | A1* | 8/2017 | Hegele | H01J 37/265 |
| | | | | 250/307 |
| 2018/0358199 | A1* | 12/2018 | Kumamoto | H01J 37/22 |

FOREIGN PATENT DOCUMENTS

| | | | | |
|---|---|---|---|---|
| JP | 2008258348 | A | 10/2008 | |
| JP | 2013160614 | A | 8/2013 | |
| JP | 2013224938 | A | 10/2013 | |
| JP | 2015237010 | * | 12/2015 | ............ H01J 37/10 |
| WO | 2015125603 | A1 | 8/2015 | |

\* cited by examiner

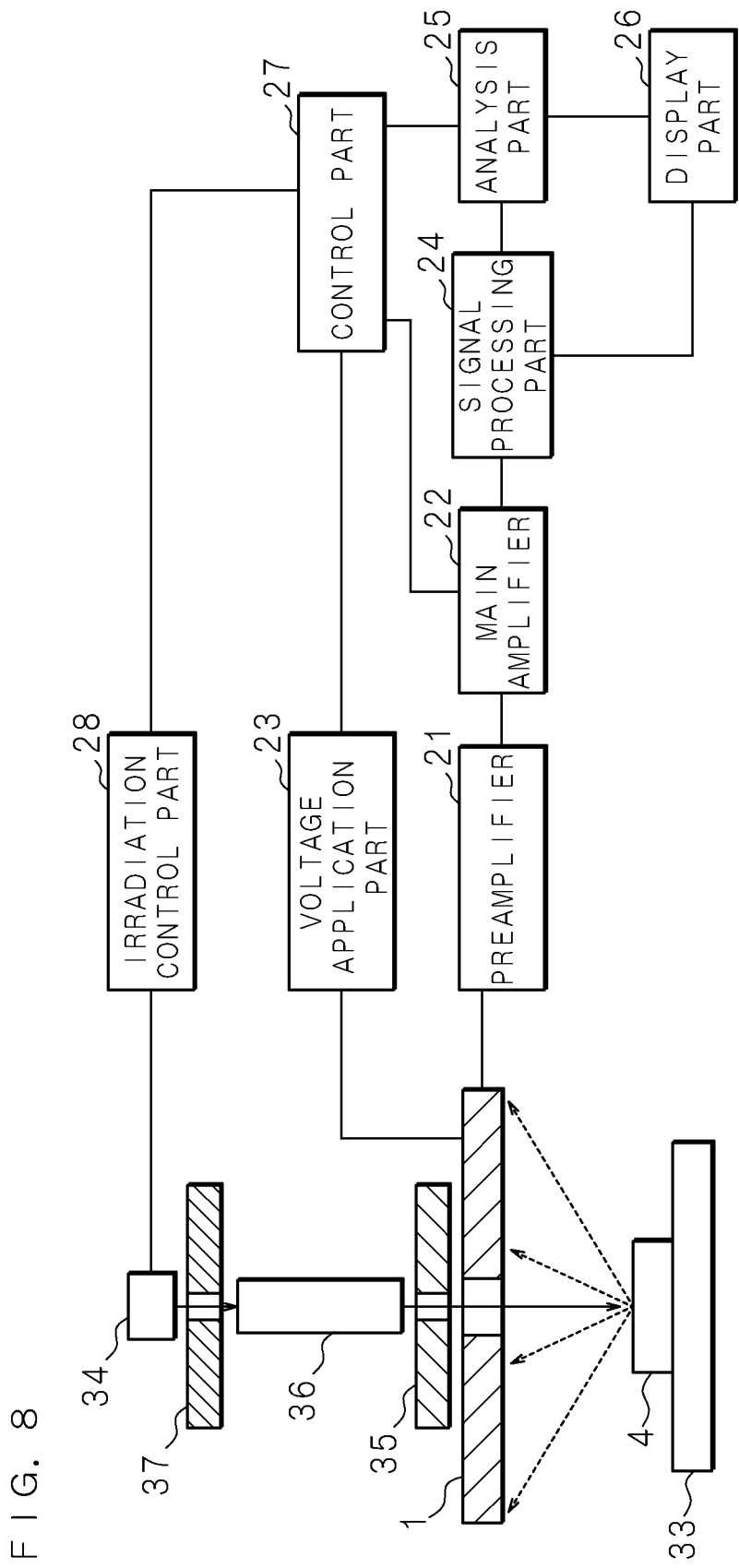

RADIATION DETECTOR AND RADIATION DETECTION APPARATUS

CROSS REFERENCE TO RELATED APPLICATION

This Application is a 371 of PCT/JP2018/020376 filed on May 28, 2018, which, in turn, claimed the priority of Japanese Patent Application No. 2017-110697 filed on Jun. 5, 2017, both applications are incorporated herein by reference.

TECHNICAL FIELD

Field

The present invention relates to a radiation detector and a radiation detection apparatus for detecting radiation.

BACKGROUND

Some radiation detectors for detecting radiation such as X-rays use semiconductor elements to detect radiation. Such radiation detectors using semiconductor elements include, for example, a silicon drift detector (SDD). An example radiation detection apparatus using a radiation detector irradiates a sample with radiation such as electron beams, X-rays or the like to detect radiation, which is generated from the sample irradiated with radiation, by the radiation detector.

To further enhance the efficiency of detecting radiation from a sample by a radiation detection apparatus, a radiation detector is preferably located closer to the sample. WO2015/125603A1 discloses a radiation detection apparatus having a plate-like radiation detector provided with a hole through which radiation to be directed to a sample passes, the radiation detector being disposed between a radiation source and the sample. The placement of the radiation detector between the radiation source and the sample can enhance the efficiency of detecting radiation by making the radiation detector closer to the sample.

SUMMARY

In a plate-like radiation detector using a radiation detection element made of semiconductor, electrodes for applying voltage to the semiconductor are arranged on both surfaces of the radiation detector. In a radiation detector provided with a hole through which radiation to be directed to a sample passes, a portion near the hole is the closest to the sample, and the radiation generated from the sample is most likely to enter the portion.

In the conventional radiation detector, however, an electrode connected to the ground potential is provided at the portion near the hole whereas an electrode for applying voltage to the semiconductor is not provided thereat. Thus, radiation that entered the portion near the hole is hardly detected. This has set a limit for enhancement in the efficiency of detecting radiation.

The present disclosure has been made in view of the above circumstances, and aims to provide a radiation detector and a radiation detection apparatus in which the efficiency of detecting radiation is enhanced by increasing a portion capable of detecting radiation.

A radiation detector according to an aspect of the present disclosure comprises a semiconductor part having a plate-like shape, the semiconductor part being provided with a through hole penetrating the semiconductor part, one surface of the semiconductor part being an incident surface for radiation. The semiconductor part has a sensitive portion capable of detecting incident radiation, and the sensitive portion includes an inner edge of the incident surface.

According to an aspect of the present disclosure, in the radiation detector, a through hole is formed at the plate-like semiconductor part, and one surface of the semiconductor part serves as an incident surface for radiation. The sensitive portion of the semiconductor part, which is capable of detecting incident radiation, includes an inner edge of the incident surface. The radiation detector is capable of detecting radiation that entered a portion on the incident surface near the through hole. Compared to the conventional case, the rate of radiation which can be detected by the radiation detector is increased.

In the radiation detector according to an aspect of the present disclosure, the sensitive portion includes an inner surface of the semiconductor part.

According to an aspect of the present disclosure, the sensitive portion of the semiconductor part includes the inner surface of the semiconductor part that is formed by the through hole being open. The radiation detector is capable of detecting radiation that entered the inner surface of the semiconductor part. Compared to the conventional case, the rate of radiation which can be detected by the radiation detector is increased.

A radiation detector according to an aspect of the present disclosure comprises a semiconductor part having a plate-like shape, the semiconductor part being provided with a through hole penetrating the semiconductor part, one surface of the semiconductor part being an incident surface for radiation. The radiation detector comprises: a first electrode continuously covering the incident surface up to an inner edge of the incident surface; and a plurality of second electrodes, provided on another surface of the semiconductor part, for applying voltage to the semiconductor part between the plurality of second electrodes and the first electrode.

According to an aspect of the present disclosure, in the radiation detector, a through hole is formed at the plate-like semiconductor part, and one surface of the semiconductor part serves as an incident surface for radiation. The radiation detector is provided with the first electrode continuously covering the incident surface of the semiconductor part up to the inner edge of the incident surface, and voltage is applied to the semiconductor part between the first electrode and the second electrodes provided on another surface of the semiconductor part, to detect radiation. By the first electrode covering the incident surface up to the inner edge, a portion of the semiconductor part including the inner edge of the incident surface serves as the sensitive portion.

The radiation detector according to an aspect of the present disclosure further includes a third electrode provided to be continuous to the first electrode and continuously covering an inner surface of the semiconductor part.

According to an aspect of the present disclosure, the radiation detector includes the third electrode which is continuous to the first electrode, the third electrode covering the inner surface of the semiconductor part. Voltage is applied to the semiconductor part between the first electrode and the second electrodes, and between the third electrode and the second electrodes, to detect radiation. By the third electrode which is continuous to the first electrode covering the inner surface of the semiconductor part, the inner surface of the semiconductor part also serves as the sensitive portion in addition to the portion including the inner edge of the incident surface.

In the radiation detector according to an aspect of the present disclosure, the plurality of second electrodes are a plurality of sets of multiple loop electrodes, and each set of the multiple loop electrodes is so configured that voltage is applied so as to change a potential in sequence, and an electrode for outputting a signal is further provided at a position surrounded by each set of multiple loop electrodes.

According to an aspect of the present disclosure, the second electrodes are sets of multiple loop electrodes. To each set of multiple loop electrodes, voltage is applied so as to change the potential in sequence. At a position surrounded by each set of multiple loop electrodes, a signal output electrode for outputting a signal is provided. Electric charge generated by radiation flows into the signal output electrode, and a signal is output from the signal output electrode. Compared to the case of one set of the multiple loop electrodes and the signal output electrode, the area of the signal output electrode is made smaller, thereby reducing electrostatic capacitance caused by the signal output electrode.

A radiation detection apparatus according to an aspect of the present disclosure comprises: an irradiation unit irradiating a sample with radiation; and the radiation detector according to an aspect of the present disclosure. The radiation detector is so arranged that radiation emitted from the irradiation unit to the sample passes through the through hole and radiation generated from the sample enters the incident surface of the semiconductor part.

According to an aspect of the present disclosure, the radiation detection apparatus irradiates a sample with radiation, and detects radiation generated from the sample by a radiation detector according to an aspect of the present disclosure. The radiation detector is so arranged that radiation directed to the sample passes through a through hole and radiation from the sample enters the incident surface of the semiconductor part. Compared to the conventional case, the rate of radiation which can be detected by the radiation detector, out of the radiation generated from the sample, is increased.

According to an aspect of the present disclosure, the efficiency of detecting radiation generated from the sample irradiated with radiation by a radiation detector is enhanced. The aspect of the present disclosure therefore produces beneficial effects of, for example, reducing the time required for detecting radiation such as characteristic X-rays or fluorescent X-rays generated from a sample.

The above and further objects and features will more fully be apparent from the following detailed description with accompanying drawings.

BRIEF DESCRIPTION OF THE DRAWINGS

FIG. 8 is a block diagram illustrating the configuration of a radiation detection apparatus according to Embodiment 3.

DETAILED DESCRIPTION

The present disclosure will specifically be described below with reference to the drawings illustrating the embodiments thereof.

Embodiment 1

Figure 1:
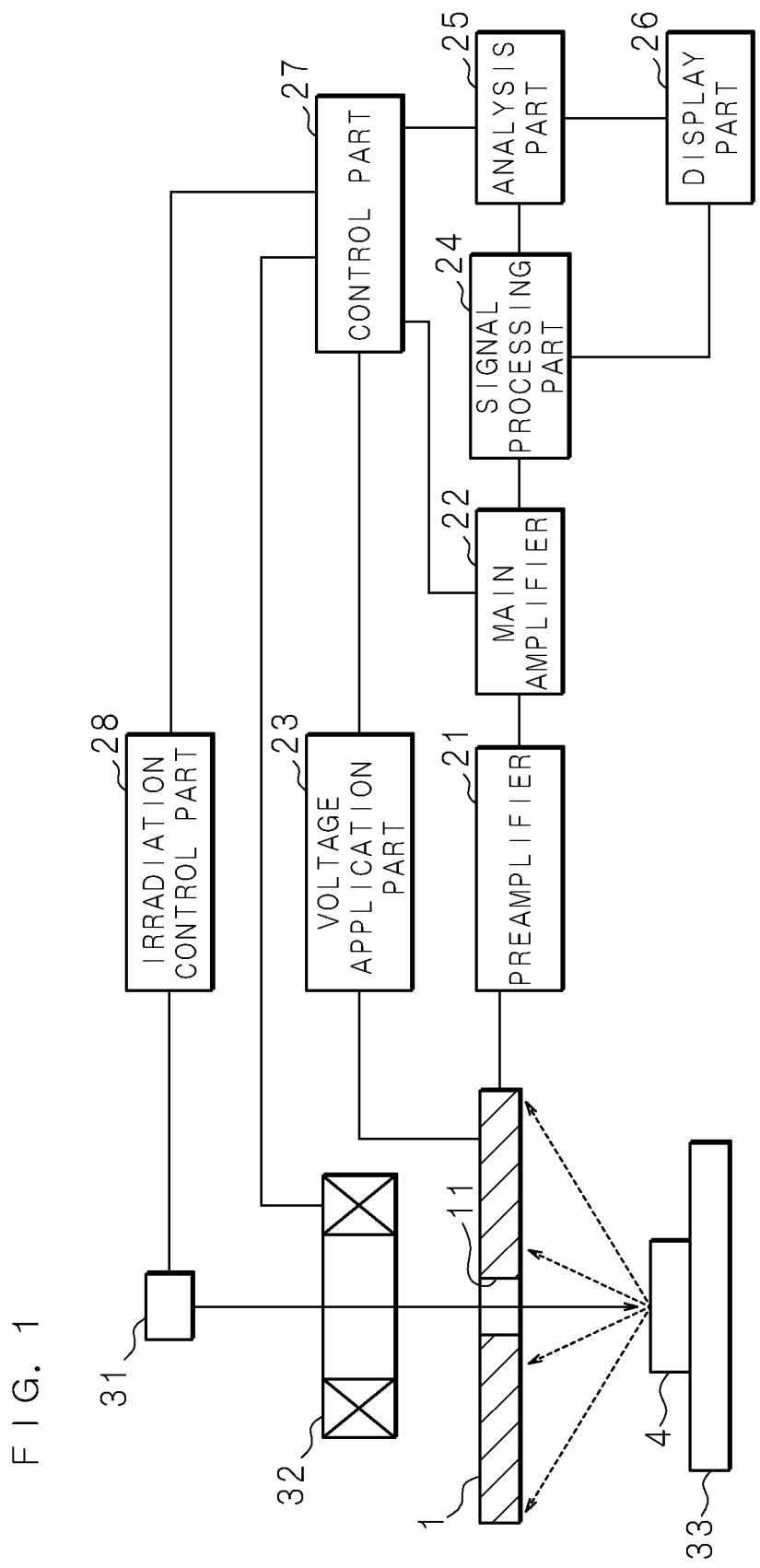
FIG. 1 is a block diagram illustrating the configuration of a radiation detection apparatus according to Embodiment 1.

FIG. 1 is a block diagram illustrating the configuration of a radiation detection apparatus according to Embodiment 1. The radiation detection apparatus irradiates a sample 4 with electron beams (radiation) and detects characteristic X-rays (radiation) generated from the sample 4 irradiated with electron beams by a radiation detector 1. For example, the radiation detection apparatus is a part of an electron microscope. The radiation detection apparatus includes an irradiation unit 31 irradiating the sample 4 with electron beams (radiation), an electron lens system 32 and a sample stage 33 on which the sample 4 is placed. The electron lens system 32 includes a scanning coil which changes the directions of electron beams. A radiation detector 1 is disposed between the electron lens system 32 and the sample stage 33. The radiation detector 1 is formed in a plate-like shape with a through hole 11 for letting through the electron beams to be directed to the sample 4. The radiation detector 1 is located at a position where electron beams can pass through the through hole 11 and is so arranged that one surface thereof faces the sample stage 33.

The radiation detector 1 is connected to the voltage application part 23 which applies voltage to the radiation detector 1 so as to allow for detecting radiation. The irradiation unit 31 is connected to an irradiation control part 28 which controls the operation of the irradiation unit 31. The voltage application part 23, irradiation control part 28 and electron lens system 32 are connected to a control part 27 which controls the entire radiation detection apparatus. The control part 27 is constituted by, for example, a personal computer. In accordance with a control signal from the control part 27, the irradiation control part 28 controls the irradiation unit 31 which emits electron beams, and the electron lens system 32 sets the directions of the electron beams which then pass through the through hole 11 of the radiation detector 1 to be directed to the sample 4 on the sample stage 33. On the sample 4, at a portion irradiated with the electron beams, characteristic X-rays are generated. The characteristic X-rays enter the radiation detector 1. In accordance with the control signal from the control part 27, the voltage application part 23 applies voltage to the radiation detector 1, which detects incident characteristic X-rays. In FIG. 1, electron beams are indicated by a solid arrow, while characteristic X-rays are indicated by broken arrows. The radiation detector 1 outputs a signal according to the detected characteristic X-rays. Among the components of the radiation detection apparatus, at least the irradiation unit 31, electron lens system 32, radiation detector 1 and sample stage 33 are housed in a vacuum box (not illustrated). The vacuum box is formed of a material which blocks electron beams and X-rays, and the inside of the vacuum box is maintained to be vacuum while the radiation detection apparatus is in operation.

Moreover, the radiation detector 1 is connected to a preamplifier 21. The preamplifier 21 is connected to a main amplifier 22. The preamplifier 21 converts the signal output from the radiation detector 1 and outputs the converted signal to the main amplifier 22. The main amplifier 22 amplifies the signal from the preamplifier 21, and outputs a signal with an intensity in accordance with the energy of the characteristic X-rays that entered the radiation detector 1. The main amplifier 22 is connected to a signal processing part 24 which processes the output signal. The signal processing part 24 counts the signals of the respective intensities output from the main amplifier 22, and performs processing of generating the relationship between the energy of the characteristic X-rays and the number of counts, i.e., the spectra of characteristic X-rays.

By the electron lens system 32 sequentially changing the directions of the electron beams, the electron beams scan the sample 4. The electron beams scanning the sample 4 allow different portions in a scanning area on the sample 4 to be irradiated with electron beams in sequence. As the electron beams scan the sample 4, the characteristic X-rays generated from the portions on the sample 4 irradiated with electron beams are sequentially detected by the radiation detector 1. The signal processing part 24 performs signal processing in sequence, to sequentially generate the spectra of characteristic X-rays generated at different portions on the sample 4 irradiated with electron beams.

The signal processing part 24 is connected to an analysis part 25. The analysis part 25 is configured to include an arithmetic operation part which performs arithmetic operation, and a memory which stores data therein. The main amplifier 22 and the analysis part 25 are connected to the control part 27. The control part 27 controls the operations of the main amplifier 22 and the analysis part 25. The signal processing part 24 sequentially outputs data indicating the generated spectra to the analysis part 25. The data from the signal processing part 24 is input to the analysis part 25, which generates spectral distribution in which the spectra indicated by the input data are associated with the positions on the sample 4 irradiated with electron beams. The analysis part 25 may also conduct a qualitative analysis or quantitative analysis of elements contained in the sample 4 based on the spectra of the characteristic X-rays, and generate the distribution of elements contained in the sample 4. The analysis part 25 is connected to a display part 26 such as a liquid crystal display. The display part 26 displays the result of the processing performed by the analysis part 25. Moreover, the display part 26 is connected to the signal processing part 24 and displays the spectra generated by the signal processing part 24. The control part 27 may be configured to accept an operation of the user and to control each part of the radiation detection apparatus in accordance with the accepted operation. Furthermore, the control part 27 and the analysis part 25 may be constituted by the same computer.

Figure 2:
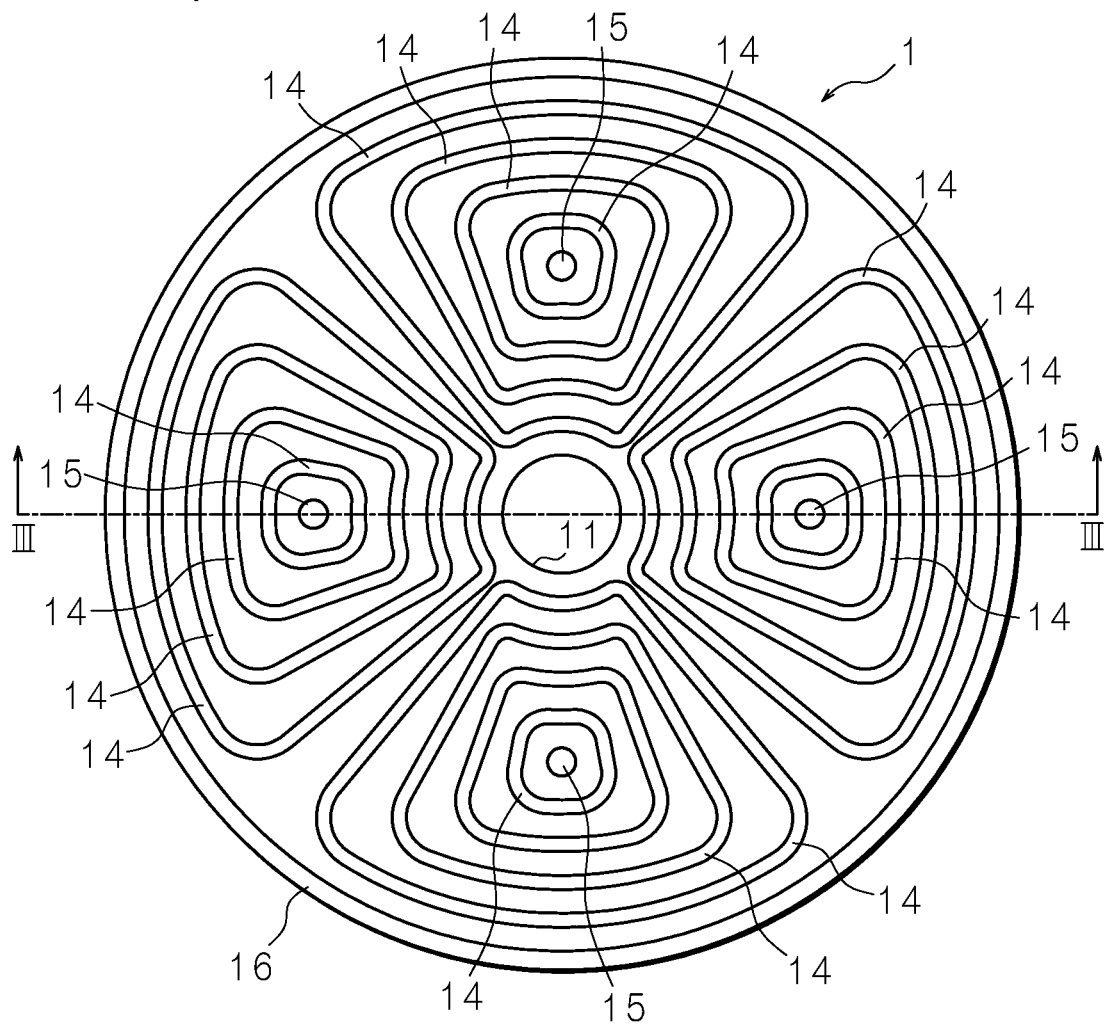
FIG. 2 is a schematic plan view of a radiation detector.
Figure 3:
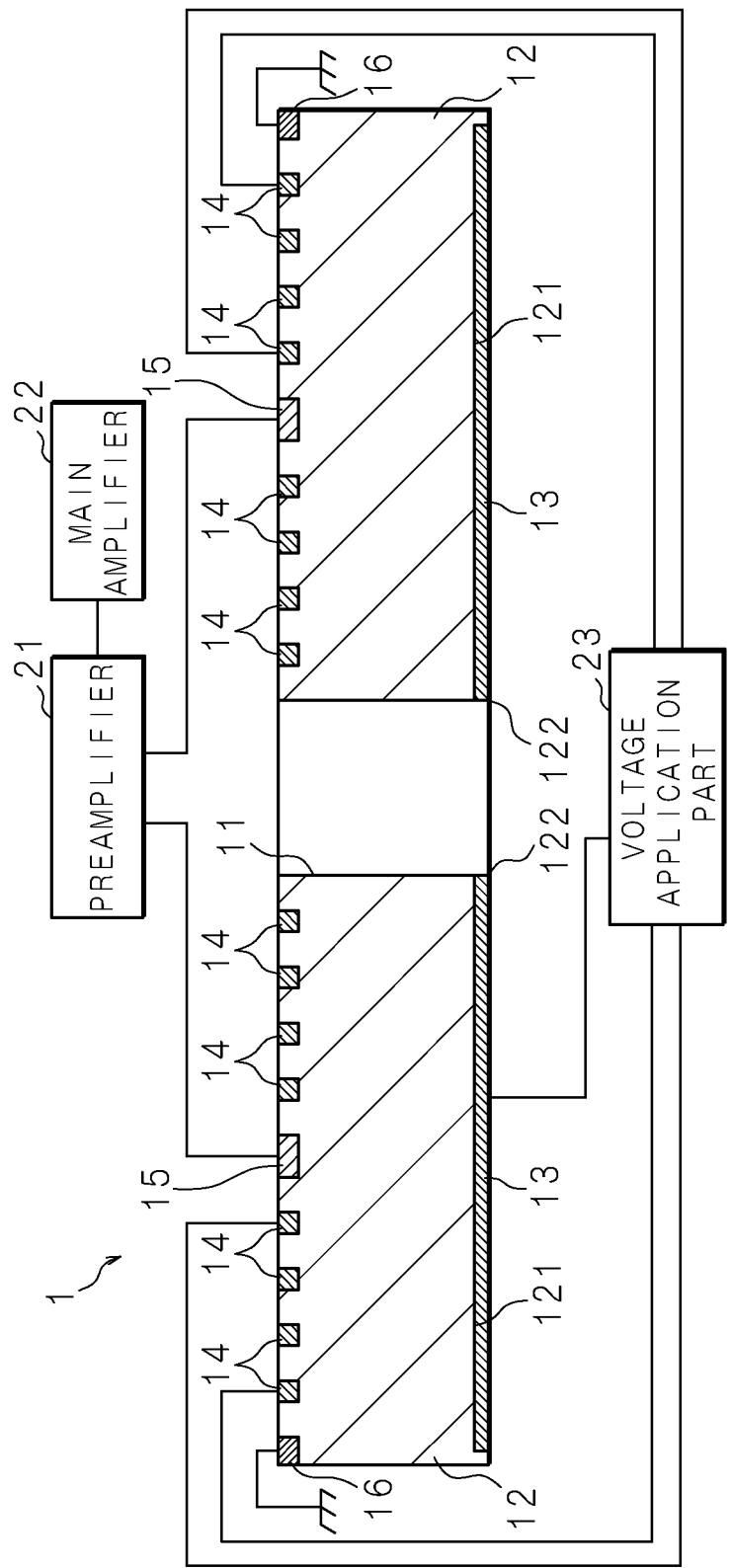
FIG. 3 is a block diagram illustrating a cross-section structure of the radiation detector according to Embodiment 1 taken along the line III-III in FIG. 2, and electrical connection of the radiation detector.

FIG. 2 is a schematic plan view of the radiation detector 1. FIG. 3 is a block diagram illustrating a cross-section structure of the radiation detector 1 according to Embodiment 1 taken along the line III-III in FIG. 2 and electrical connection of the radiation detector 1. The radiation detector 1 is constituted by combining multiple radiation detection elements. The present embodiment illustrates an example where a radiation detection element is an SDD. The radiation detector 1 includes a semiconductor part 12 having a disc-shape and made of silicon (Si). The semiconductor part 12 is made of, for example, n-type Si. A through hole 11 penetrating the semiconductor part 12 in the direction intersecting the surface thereof is formed in the middle of the semiconductor part 12. One surface of the semiconductor part 12 serves as an incident surface 121 for radiation. The surface on the lower side of the semiconductor part 12 illustrated in FIG. 3 is the incident surface 121, whereas the surface on the upper side thereof is a back surface. FIG. 2 illustrates the radiation detector 1 viewed from the back side of the semiconductor part 12. The semiconductor part 12 may have a shape other than the disc shape, such as a square.

The radiation detector 1 is provided with a first electrode 13 which continuously covers the incident surface 121 of the semiconductor part 12. The first electrode 13 covers at least a peripheral portion of the through hole 11 on the incident surface 121, and covers up to an inner edge 122 of the incident surface 121. The inner edge 122 is formed by the through hole 11 being open in the semiconductor part 12. The inner edge 122 is an edge of the semiconductor part 12 that is included in the peripheral portion of the through hole 11 on the incident surface 121. The first electrode 13 is made of Si of a type different from that of the semiconductor part 12. For example, if the semiconductor part 12 is made of n-type Si, the first electrode 13 is made of p+Si. The first electrode 13 is connected to the voltage application part 23.

As illustrated in FIG. 2, sets of multiple second electrodes 14 having a loop-like shape are provided on the back surface of the semiconductor part 12. FIG. 2 illustrates an example where four sets of multiple second electrodes 14 are provided. The number of sets of multiple second electrodes 14 is not limited to four, but may be eight or a different number. The sets of multiple second electrodes 14 are evenly arranged around the through hole 11. One set of multiple second electrodes 14 are included in one SDD.

That is, a multiple number of SDDs are arranged around the through hole 11. The multiple second electrodes 14 in each set are arranged at substantially equal intervals. While FIG. 2 illustrates an example where four second electrodes 14 are included in each set, a larger number of second electrodes 14 are provided in practice. The second electrode 14 is made of, for example, p+Si in which Si is doped with specific impurities such as boron. It is noted that the sets of multiple second electrodes 14 may be unevenly arranged around the through hole 11. Moreover, the multiple second electrodes 14 in each set may be arranged at unequal intervals.

At a position surrounded by each set of multiple second electrodes 14, a signal output electrode 15 is provided, which is an electrode that outputs signals at the time of detecting radiation. The signal output electrode 15 is made of, for example, Si of the same type as that of the semiconductor part 12, which is doped with specific impurities such as phosphorus. The signal output electrode 15 is connected to the preamplifier 21. Among the multiple second electrodes 14 in each set, the second electrode 14 which is the closest to the signal output electrode 15 and the second electrode 14 which is the farthest from the signal output electrode 15 are connected to the voltage application part 23. A ground electrode 16 connected to the ground potential is provided near an outer periphery of the radiation detector 1. Furthermore, the radiation detector 1 may include a cooling mechanism (not illustrated) such as a Peltier device.

The voltage application part 23 applies voltage to each set of the multiple second electrodes 14 such that the second electrode 14 which is the closest to the signal output electrode 15 has the highest potential whereas the second electrode 14 which is the farthest to the signal output electrode 15 has the lowest potential. Moreover, the radiation detector 1 is so configured that a predetermined electric resistance is generated between adjacent second electrodes 14. For example, by adjusting a chemical component of one portion of the semiconductor part 12 located between adjacent second electrodes 14, an electric resistance channel is formed through which the two second electrodes 14 are connected with each other. That is, the multiple second electrodes 14 in each set are linked together through the electric resistance. By applying voltage from the voltage application part 23 to such multiple second electrodes 14, the second electrodes 14 have potentials monotonously increasing in sequential order from the second electrode 14 which is the farthest from the signal output electrode 15 toward the second electrode 14 which is the closest to the signal output electrode 15. The second electrodes 14 may include a pair of adjacent second electrodes 14 with the same potential. Based on the potential of the second electrodes 14, an electric field is generated in which the potential is higher at a position closer to the signal output electrode 15 and is lower at a position farther from the signal output electrode 15 in the semiconductor part 12. Furthermore, the voltage application part 23 applies voltage to the first electrode 13 such that the first electrode 13 has a potential lower than that of the second electrode 14 with the highest potential in each set. Accordingly, voltage is applied to the semiconductor part 12 between the first electrode 13 and the second electrodes 14, and in the semiconductor part 12, such an electric field is generated that the potential becomes higher as it approaches closer to the signal output electrode 15.

The radiation detector 1 is located such that the incident surface 121 faces the placement surface of the sample stage 33. That is, in the state where the sample 4 is placed on the sample stage 33, the incident surface faces the sample 4. The characteristic X-rays from the sample 4 pass through the first electrode 13 and enters inside the semiconductor part 12 through the incident surface 121. The characteristic X-rays are absorbed by the semiconductor part 12, and electric charge of an amount corresponding to the energy of the absorbed characteristic X-rays is generated. The generated electric charge includes electrons and holes. The generated electric charge moves by the electric field inside the semiconductor part 12, and one type of the charge flows into the closest signal output electrode 15. According to the present embodiment, if the signal output electrode 15 is of the n type, the electrons generated by incident radiation move and flow into the signal output electrode 15. The charge flowing into the signal output electrode 15 is output as a current signal, and is input to the preamplifier 21. The preamplifier 21 converts the current signal into a voltage signal and outputs the converted voltage signal to the main amplifier 22. The main amplifier 22 amplifies the voltage signal from the preamplifier 21, and outputs a signal with an intensity in accordance with the energy of the radiation that entered the radiation detector 1.

Since the radiation detector 1 includes plural sets of multiple second electrodes 14 and signal output electrode 15, the ratio (SN ratio) of a signal (S) output by the preamplifier 21 to noise (N) of the preamplifier 21 is increased compared to the case of one set of the multiple second electrodes 14 and signal output electrode 15. In the case where one set of the multiple second electrodes 14 and the signal output electrode 15 is employed, the signal output electrode 15 is formed in a ring-like shape. Compared with this case, the radiation detector 1 including plural sets of the multiple second electrodes 14 and the signal output electrode 15 has a smaller area of the signal output electrode 15. As the area of the signal output electrode 15 is made smaller, the electrostatic capacitance of the preamplifier 21 caused by the signal output electrode 15 is reduced. As the capacitance is reduced, the voltage obtained from a specific charge is increased, thereby increasing the SN ratio of the voltage signal to be output by the preamplifier 21.

Figure 4:
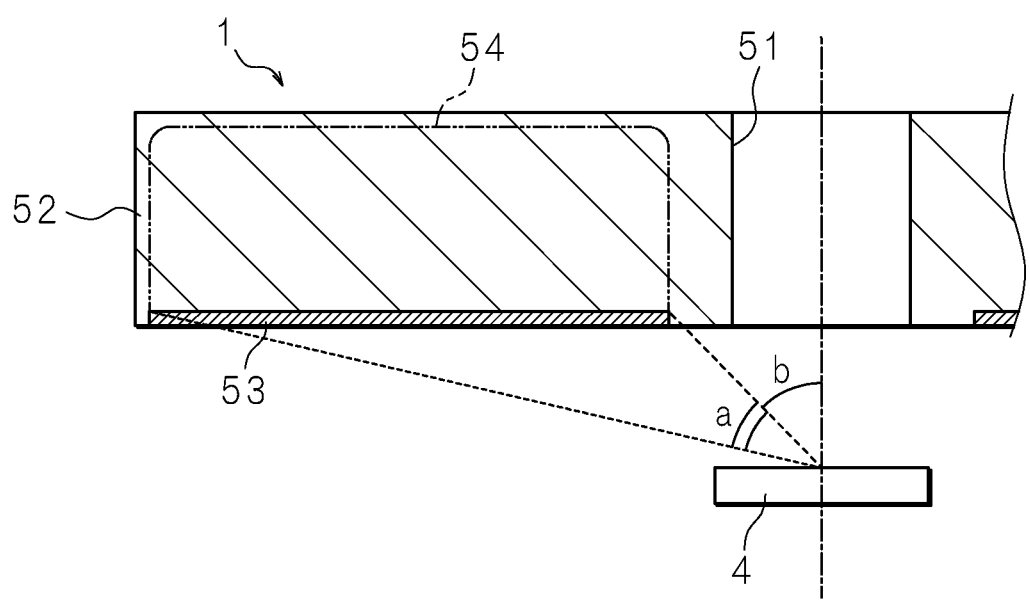
FIG. 4 is a schematic cross-section view illustrating the positional relationship between the conventional radiation detector and a sample.
Figure 5:
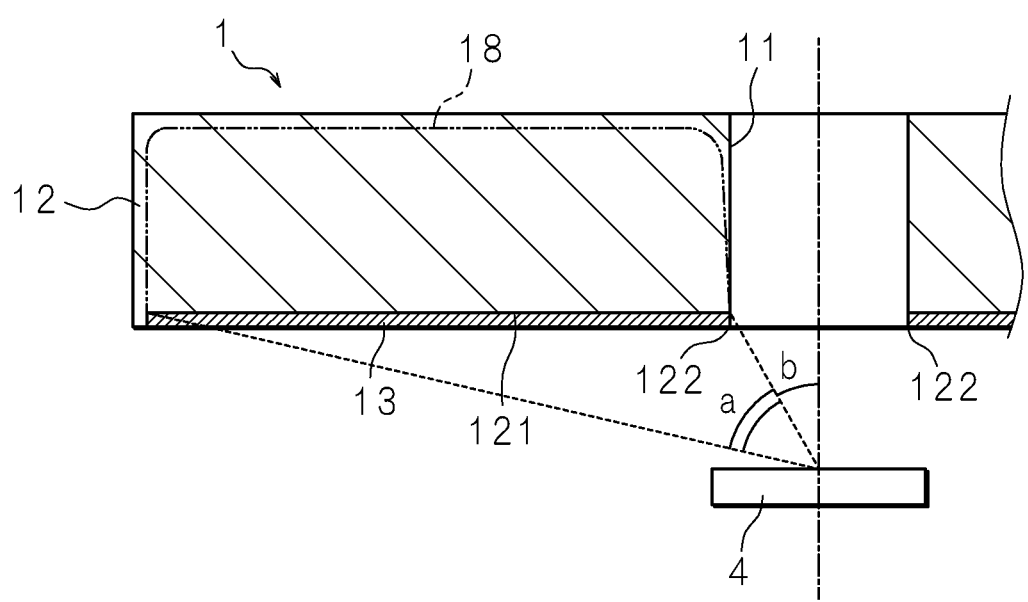
FIG. 5 is a schematic cross-section view illustrating the positional relationship between the radiation detector according to Embodiment 1 and a sample.

The radiation detector 1 according to the present embodiment is compared with the conventional radiation detector. FIG. 4 is a schematic cross-section view illustrating the positional relationship between the conventional radiation detector and the sample 4. FIG. 5 is a schematic cross-section view illustrating the positional relationship between the radiation detector 1 according to Embodiment 1 and the sample 4. In FIG. 4, for the conventional radiation detector, the through hole is denoted by 51, the semiconductor part is denoted by 52 and the first electrode is denoted by 53. In FIG. 4 and FIG. 5, components of the radiation detector excluding the through hole, semiconductor part and first electrode are not illustrated. Furthermore, FIG. 4 and FIG. 5 illustrate the cross-section passing the center line of the through hole, while the center line is indicated by a dashed-dotted line.

As illustrated in FIG. 4, in the conventional radiation detector, a portion of the incident surface of the semiconductor part 52 that is near the inner edge of the incident surface is not covered by the first electrode 53. A sensitive portion 54 in the semiconductor part 52 that is capable of detecting incident radiation is a portion where an electric field is generated such that electric charge flows toward a signal output electrode (not illustrated) by applying voltage to the first electrode 53. The sensitive portion 54 is a portion included between the dashed-two dotted line in FIG. 4 and the first electrode 53. A portion of the incident surface of the semiconductor part 52 that is not covered by the first electrode 53 is not included in the sensitive portion 54, since the electric field in which electric charge flows toward the signal output electrode is not generated in such a portion. Thus, a portion of the incident surface of the semiconductor part 52 that is near the inner edge is not included in the sensitive portion 54.

As illustrated in FIG. 5, in the radiation detector 1 according to the present embodiment, the first electrode 13 covers the incident surface 121 of the semiconductor part 12 up to the inner edge 122 of the incident surface 121. A sensitive portion 18 in the semiconductor part 12 that is capable of detecting incident radiation is a portion included between the dashed-two dotted line in FIG. 5 and the first electrode 13. Since voltage is applied to the first electrode 13 also at the portion on the incident surface 121 including the inner edge 122, an electric field is generated such that electric charge flows toward the signal output electrode 15, and therefore this portion is included in the sensitive portion 18. That is, in the radiation detector 1 according to the present embodiment, the sensitive portion 18 is expanded compared to the conventional radiation detector. The portion near the inner edge 122 of the incident surface 121 is the closest to the sample 4 among different portions of the incident surface 121. Thus, this portion is included in the sensitive portion 18, thereby increasing the solid angle of the area where the characteristic X-rays entering the sensitive portion 18 of the semiconductor part 12 among the characteristic X-rays generated at the sample 4 pass through. Here, the solid angle of the area where the characteristic X-rays entering the sensitive portion 18 of the semiconductor part 12 pass through is referred to as an effective solid angle a.

The effective solid angle a is changed by the distance between the radiation detector and the sample 4. The distance at which the effective solid angle a is maximum is obtained geometrically. In the present embodiment, the maximum effective solid angle a is significantly increased compared to the conventional case. In the radiation detector 1 having the outer diameter of 18 mm with the through hole 11 having the diameter of 3 mm, the effective solid angle a is 3.7 (steradian) in the state where the effective solid angle a is maximum. Moreover, as illustrated in FIG. 4 and FIG. 5, in the cross section passing the center line of the through hole, an angle b around the center line of the through hole in an area where the characteristic X-rays not entering the sensitive portion pass is smaller in the present embodiment than the conventional case. The angle b in the state where the effective solid angle a is maximum is larger than 40 degrees in the conventional radiation detector, whereas it is 40 degrees or smaller in the present embodiment. Furthermore, in the case where the radiation detection apparatus operates by a general method of scanning the sample 4 with electronic beams, the diameter of the through hole 11 may be as small as 0.5 mm. The minimum value of the angle b in the case where the diameter of the through hole 11 is 0.5 mm is 14 degrees.

As specifically described above, according to the present embodiment, the first electrode 13 covers the incident surface 121 of the semiconductor part 12 up to the inner edge 122 of the incident surface 121, so that the inner edge 122 of the incident surface 121 is also included in the sensitive portion 18. Compared to the conventional case, the sensitive portion 18 is increased in a region near the sample 4, thereby significantly increasing the effective solid angle of the area where the characteristic X-rays entering the sensitive portion 18 among the characteristic X-rays generated at the sample 4 pass through. The increase of the effective solid angle also increases the rate of the characteristic X-rays which can be detected by the radiation detector 1 among the characteristic X-rays generated from the sample 4, and thus enhances the efficiency of detecting characteristic X-rays. The enhancement in the efficiency of detecting characteristic X-rays may shorten the time required for detecting the characteristic X-rays generated from the sample 4. In addition, the time required for scanning the sample 4 is shortened, while the time required for analyzing the sample 4 is also shortened.

Embodiment 2

Figure 6:
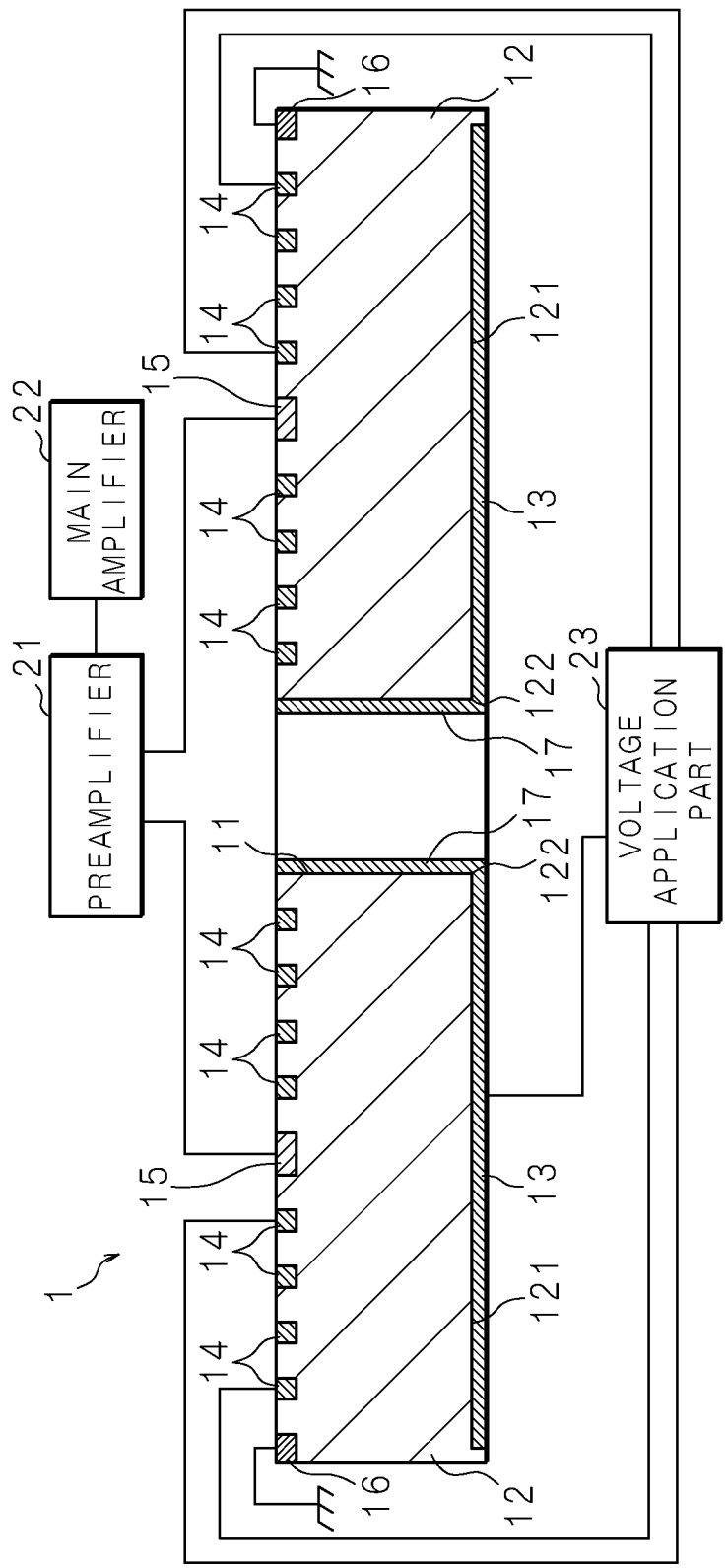
FIG. 6 is a block diagram illustrating a cross-section structure of the radiation detector according to Embodiment 2 and electrical connection of the radiation detector.

FIG. 6 is a block diagram illustrating a cross-section structure of the radiation detector 1 according to Embodiment 2 and electrical connection of the radiation detector 1. As in Embodiment 1, the radiation detector 1 is provided with a first electrode 13 which continuously covers the incident surface 121 of the semiconductor part 12 up to the inner edge 122 of the incident surface 121. Furthermore, the radiation detector 1 is provided with a third electrode 17 which continuously covers the inner surface of the semiconductor part 12. The inner surface of the semiconductor part 12 is formed by the through hole 11 being open in the semiconductor part 12. The inner surface is the surface of the semiconductor part 12 surrounding the through hole 11. The third electrode 17 is continuous with the first electrode 13. On the inner surface of the semiconductor part 12, the third electrode 17 covers at least a portion which is continuous from the incident surface 121. The voltage application part 23 applies voltage to the first electrode 13 and the third electrode 17 such that the first electrode 13 and the third electrode 17 have the potential lower than that of the second electrode 14 with the lowest potential in each set. Accordingly, voltage is applied to the semiconductor part 12 between the first electrode 13 and the second electrodes 14, and between the third electrode 17 and the second electrodes 14, and an electric field is generated in the semiconductor part 12. The other components and functions of the radiation detector 1 is similar to those in Embodiment 1. Moreover, components other than the radiation detector 1 in the radiation detection apparatus are similar to those in Embodiment 1.

Figure 7:
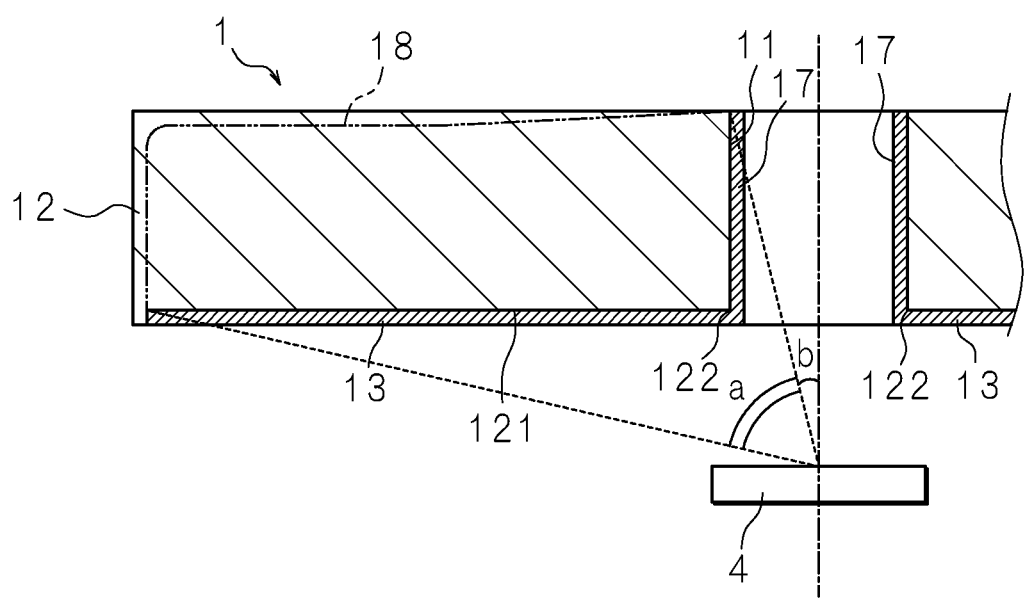
FIG. 7 is a schematic cross-section view illustrating the positional relationship between the radiation detector according to Embodiment 2 and a sample.

FIG. 7 is a schematic cross-section view illustrating the positional relationship between the radiation detector 1 according to Embodiment 2 and the sample 4. According to the present embodiment, since the inner surface of the semiconductor part 12 is covered with the third electrode 17 and voltage is also applied to the third electrode 17 by the voltage application part 23, an electric field is generated also at the inner surface of the semiconductor part 12. Thus, the sensitive portion 18 of the semiconductor part 12, that is capable of detecting incident radiation, includes an inner surface of the semiconductor part 12. The sensitive portion 18 is a portion included between the dashed-two dotted line in FIG. 7 and the first electrode 13, and between the dashed-two dotted line and the third electrode 17. The inner surface of the semiconductor part 12 is formed by a method in that deformation is not likely to remain in the crystal structure, such as etching. Of the characteristic X-rays generated at the sample 4, the characteristic X-rays passing through the third electrode 17 and entering the semiconductor part 12 from the inner surface of the semiconductor part 12 are detected. According to the present embodiment, as the sensitive portion 18 also includes the inner surface of the semiconductor part 12, the effective solid angle a of the area where the characteristic X-rays entering the sensitive portion 18 of the semiconductor part 12 pass through is further increased. In the radiation detector 1 according to the present embodiment having the outer diameter of 18 mm with the through hole 11 having the diameter of 3 mm, the effective solid angle a is 4.0 (steradian) in the state where the effective solid angle a is maximum. Moreover, as illustrated in FIG. 7, in the cross section passing the center line of the through hole 11, an angle b around the center line of the through hole 11 in an area where the characteristic X-rays not entering the sensitive portion 18 pass is 40 degrees or smaller also in the present embodiment. Furthermore, in the present embodiment also, in the case where the radiation detection apparatus operates by a general method of scanning the sample 4 with electronic beams, the diameter of the through hole 11 may be as small as 0.5 mm. The minimum value of the angle b in the case where the diameter of the through hole 11 is 0.5 mm is 9 degrees.

As specifically described above, according to the present embodiment, by the third electrode 17 which is continuous to the first electrode 13 covering the inner surface of the semiconductor part 12, the inner surface of the semiconductor part 12 is also included in the sensitive portion 18 in addition to the portion including the inner edge 122 on the incident surface 121. The sensitive portion 18 is increased compared to Embodiment 1, and the effective solid angle of the area where the characteristic X-rays entering the sensitive portion 18, of the characteristic X-rays generated at the sample 4, pass through is further increased. This also increases the rate of the characteristic X-rays which can be detected by the radiation detector 1 among the characteristic X-rays generated from the sample 4, and thus enhances the efficiency of detecting characteristic X-rays. The time required for detecting characteristic X-rays is shortened, while the time required for analyzing the sample 4 is also shortened. While the present embodiment illustrated the form where the third electrode 17 covers the entire inner surface of the semiconductor part 12, the radiation detection apparatus may also take a form where the third electrode 17 covers a part of the inner surface of the semiconductor part 12.

It is noted that the radiation detection apparatus may also take a form where the second electrode 14 which is the closest to the through hole 11 in each set is connected to the first electrode 13 and the third electrode 17. In this form, the second electrode 14 which is the closest to the through hole 11 has the same potential as that of the first electrode 13 and the third electrode 17. The voltage application part 23 applies voltage to the first electrode 13 and the third electrode 17 such that the first electrode 13 and the third electrode 17 have the potential lower than that of the other second electrodes 14.

Embodiment 3

FIG. 8 is a block diagram illustrating the configuration of a radiation detection apparatus according to Embodiment 3. The radiation detection apparatus includes an irradiation unit 34 irradiating the sample 4 with X-rays, but does not include the irradiation unit 31 emitting electron beams and the electron lens system 32. The irradiation unit 34 is configured with an X-ray tube. Furthermore, the radiation detection apparatus includes a converging part 36 which is an optical system that converges X-rays emitted by the irradiation unit 31. For example, the converging part 36 is made of a polycapillary. A first collimator 35 which limits the irradiation range of X-rays is arranged between the converging part 36 and the radiation detector 1, whereas a second collimator 37 is arranged between the irradiation unit 34 and the converging part 36. The radiation detector 1 is disposed between the converging part 36 and the sample stage 33. The radiation detector 1 is configured similarly to that in Embodiment 1 or 2. The other configuration of the radiation detector 1 is similar to that in Embodiment 1 or 2.

The irradiation unit 34 irradiates the sample 4 on the sample stage 33 with X-rays. The X-rays emitted from the irradiation unit 34 are narrowed down by the second collimator 37, is converged at the converging part 36, narrowed down by the first collimator 35 and pass through the through hole 11 of the radiation detector 1 to be directed to the sample 4. Furthermore, the first collimator 35 prevents the radiation detector 1 from being directly irradiated with the X-rays from the irradiation unit 34. The irradiation of X-rays allows the sample 4 to generate fluorescent X-rays. In FIG. 8, the X-rays directed to the sample 4 are indicated by a solid arrow, while the fluorescent X-rays are indicated by broken arrows. The radiation detector 1 detects generated fluorescent X-rays. The signal processing part 24 obtains the spectra of the fluorescent X-rays. The analysis part 25 performs processing of an analysis based on the spectra of the fluorescent X-rays. Note that the radiation detection apparatus may also take a form of including a mechanism for moving the sample 4 in the horizontal direction, scanning the sample 4 with the X-ray beams from the irradiation unit 34 and generating the spectral distribution of fluorescent X-rays. Moreover, the radiation detection apparatus may take a form of excluding the second collimator 37. Moreover, the radiation detection apparatus may take a form where the first collimator 35 is excluded and the lower end of the converging part 36 is inserted into the through hole 11 of the radiation detector 1.

In the present embodiment also, as in Embodiment 1 or 2, the sensitive portion 18 capable of detecting radiation is increased in the semiconductor part 12 compared to the conventional case. The increase of the sensitive portion 18 also increases the effective solid angle of the area where the fluorescent X-rays entering the sensitive portion 18, of the fluorescent X-rays generated at the sample 4, pass through is further increased. This also increases the rate of the fluorescent X-rays which can be detected by the radiation detector 1 among the fluorescent X-rays generated from the sample 4, and thus enhances the efficiency of detecting fluorescent X-rays. The time required for detecting fluorescent X-rays is shortened, while the time required for analyzing the sample 4 is also shortened.

While Embodiments 1 to 3 above illustrated examples where the semiconductor part 12 is made of an n-type semiconductor and the second electrode 14 is made of a p-type semiconductor, the radiation detector 1 may also take a form where the semiconductor part 12 is made of a p-type semiconductor and the second electrode 14 is made of an n-type semiconductor. Furthermore.

Embodiments 1 to 3 mainly illustrated examples where electrons generated by radiation flow into the signal output electrode 15, while the radiation detector 1 may also take a form where holes generated by radiation flow into the signal output electrode 15. In this form, the voltage application part 23 applies voltage to the second electrodes 14 such that the potential monotonously decreases in sequential order from the second electrode 14 which is far from the signal output electrode 15 toward the second electrode 14 which is close to the signal output electrode 15. In the case of not including the third electrode 17, the voltage application part 23 applies voltage to the first electrode 13 such that the first electrode 13 has a potential higher than that of the second electrode 14 with the lowest potential in each set. In the case where the third electrode 17 is provided and where the second electrode 14 is not connected to the third electrode 17, the voltage application part 23 applies voltage to the first electrode 13 and the third electrode 17 such that the first electrode 13 and the third electrode 17 have the potential higher than that of the second electrode 14 with the highest potential in each set. In the case where the second electrode 14 which is the closest to the through hole 11 is connected to the third electrode 17, the voltage application part 23 applies voltage to the first electrode 13 and the third electrode 17 such that the first electrode 13 and the third electrode 17 have the potential higher than that of the other second electrodes 14.

While Embodiments 1 to 3 illustrated examples where the second electrode 14 has a loop-like shape, the radiation detector 1 may also take a form of including multiple second electrodes 14 having an arcuate shape. The radiation detector 1 may take a form of including a guard part preventing dielectric breakdown between the second electrodes 14 and the ground electrode 16. The guard part has a ring-like shape, and is located between the second electrode 14 farthest from the signal output electrode 15 and the ground electrode 16. The guard part is made of the same material as the second electrode 14. The guard part is not connected to the voltage application part 23. The potential of the guard part is a floating potential. The guard part prevents dielectric breakdown between the second electrode 14 farthest from the signal output electrode 15 and the ground electrode 16. Moreover, while Embodiments 1 to 3 illustrated examples where the ground electrode 16 is provided near the outer periphery of the radiation detector 1, the radiation detector 1 may also take a form of not including the ground electrode 16. The radiation detector 1 may also take a form where the first electrode 13 covers the incident surface 121 to the outer periphery. Furthermore, while Embodiments 1 to 3 illustrated examples where the radiation detector 1 is constituted by an SDD, the radiation detector 1 may also take a form of being constituted by an element other than SDD as long as the sensitive portion 18 includes the inner edge 122 of the incident surface 121. While Embodiments 1 and 2 illustrated examples where the sample 4 is irradiated with electron beams and Embodiment 3 illustrated an example where the sample 4 is irradiated with X-rays, the radiation detection apparatus may also take a form of irradiating the sample 4 with radiation other than electron beams or X-rays. Furthermore, while Embodiments 1 to 3 illustrated examples where X-rays are detected by the radiation detector 1, the radiation detection apparatus may also take a form of detecting radiation other than X-rays by the radiation detector 1.

It is to be noted that, as used herein and in the appended claims, the singular forms "a", "an", and "the" include plural referents unless the context clearly dictates otherwise.

It is to be noted that the disclosed embodiment is illustrative and not restrictive in all aspects. The scope of the present invention is defined by the appended claims rather than by the description preceding them, and all changes that fall within metes and bounds of the claims, or equivalence of such metes and bounds thereof are therefore intended to be embraced by the claims.

What is claimed is:

1. A radiation detector, comprising:
   a semiconductor part having an incident surface for radiation and a back surface; and
   the semiconductor part including a through hole penetrating from the incident surface to the back surface, wherein
   the semiconductor part has a sensitive portion capable of detecting incident radiation, and
   the sensitive portion includes an inner edge that is an edge of a peripheral portion of the through hole on the incident surface.
2. The radiation detector according to claim 1, wherein the sensitive portion includes an inner surface that is a surface of the semiconductor part surrounding the through hole.
3. A radiation detector, comprising:
   a semiconductor part having an incident surface for radiation and a back surface;
   the semiconductor part including a through hole penetrating from the incident surface to the back surface;
   a first electrode continuously covering the incident surface up to an inner edge that is an edge of a peripheral portion of the through hole on the incident surface; and
   a plurality of second electrodes, provided on the back surface of the semiconductor part, for applying voltage to the semiconductor part between the plurality of second electrodes and the first electrode.
4. The radiation detector according to claim 3, further comprising
   a third electrode provided to be continuous to the first electrode and continuously covering an inner surface that is a surface of the semiconductor part surrounding the through hole.
5. The radiation detector according to claim 3, wherein the plurality of second electrodes are a plurality of sets of multiple loop electrodes, and
   each set of the multiple loop electrodes is so configured that voltage is applied so as to change a potential in sequence, and
   a signal output electrode for outputting a signal is further provided at a position surrounded by each set of multiple loop electrodes.
6. A radiation detection apparatus, comprising:
   an irradiation unit irradiating a sample with radiation; and
   the radiation detector according to claim 1,
   wherein the radiation detector is so arranged that radiation emitted from the irradiation unit to the sample passes through the through hole and radiation generated from the sample enters the incident surface of the semiconductor part.
7. A radiation detection apparatus, comprising:
   an irradiation unit irradiating a sample with radiation; and
   the radiation detector according to claim 3,
   wherein the radiation detector is so arranged that radiation emitted from the irradiation unit to the sample passes through the through hole and radiation generated from the sample enters the incident surface of the semiconductor part.
8. The radiation detection apparatus according to claim 6, wherein
   an angle between a center line of the through hole and a line intersecting the center line at the sample and where the radiation does not enter the sensitive portion is 40 degrees or smaller.
9. The radiation detection apparatus according to claim 7, wherein
   an angle between a center line of the through hole and a line intersecting the center line at the sample and where radiation does not enter the first electrode is 40 degrees or smaller.
10. The radiation detector according to claim 5, wherein voltage is applied to the multiple loop electrodes of each set of the plurality of sets so that an electrode of the multiple loop electrodes that is closest to the signal output electrode has a highest potential and an electrode of the multiple loop electrodes that is farthest from the signal output electrode has a lowest potential.
11. The radiation detector according to claim 10, wherein the electrode of the multiple loop electrodes that is farthest from the signal output electrode of the each set of the plurality of sets and the first electrode have the same potential.

* * * * *